United States Patent [19]

Patis

[11] 4,350,885
[45] Sep. 21, 1982

[54] BATTERY HYDROMETER WITH ANALOG OUTPUT

[75] Inventor: Bruce L. Patis, Addison, Ill.

[73] Assignee: Illinois Tool Works Inc., Chicago, Ill.

[21] Appl. No.: 191,785

[22] Filed: Sep. 29, 1980

[51] Int. Cl.³ .............................................. G01N 9/00
[52] U.S. Cl. .................................. 250/231 R; 73/453
[58] Field of Search ....................... 250/231 R, 231 P; 73/453; 429/90, 91, 92, 93

[56] References Cited

U.S. PATENT DOCUMENTS 2,981,111  4/1961  McIlwraith ........................... 73/453

*Primary Examiner*—David C. Nelms
*Assistant Examiner*—Darwin R. Hostetter
*Attorney, Agent, or Firm*—Jerold M. Forsberg; Thomas W. Buckman; Jack R. Halvorsen

[57] ABSTRACT

There is disclosed a battery hydrometer for providing an analog electrical signal having a magnitude related to the specific gravity of a battery electrolyte. The hydrometer includes a source of radiation for providing a detectable beam of radiation and a piston member arranged to be submerged within the electrolyte and to intercept and modulate the beam of radiation in response to the specific gravity of the electrolyte. The piston member is suspended within the electrolyte by a spring which exerts a compressive force upon the piston member against which the electrolyte must act. The hydrometer further includes a radiation detector aligned with the radiation source for providing an analog electrical signal having a magnitude responsive to the modulated beam of radiation.

18 Claims, 1 Drawing Figure

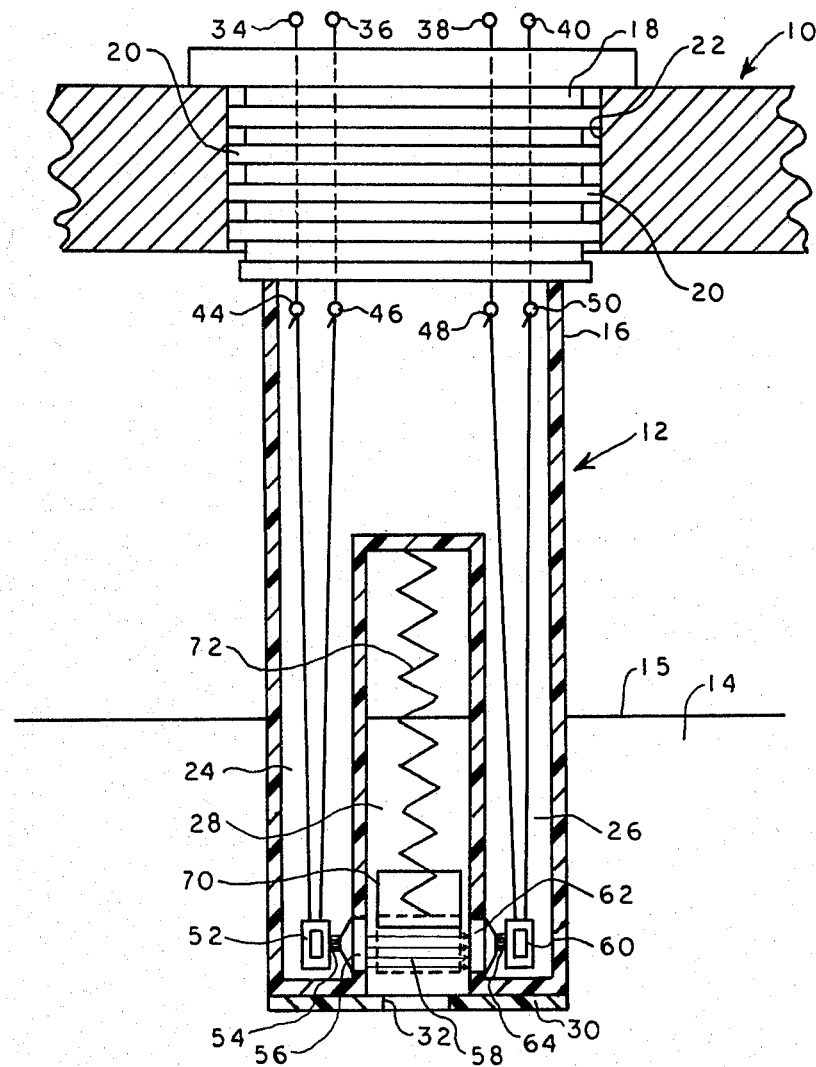

BATTERY HYDROMETER WITH ANALOG OUTPUT

BACKGROUND OF THE INVENTION

The present invention is generally directed to battery hydrometers and more particularly to a battery hydrometer which provides an analog output electrical signal related to the specific gravity of the battery electrolyte and therefore related to the state of charge of the battery.

Battery hydrometers for indicating whether a battery is adequately charged or in need of recharging have taken many forms. In one form, an elongated light transmitting rod having an external viewing surface and a conical tip arranged to be disposed beneath the surface of the electrolyte is associated with a float, generally a ball of a bright color, confined within an open walled cage. The cage is carried at the end of the rod and is arranged to dispose the float in two different positions relative to the rod tip depending upon the specific gravity of the battery electrolyte. In one position, the ball is immediately adjacent the tip and viewable through the indicating surface. This indicates that the specific gravity of the electrolyte is above a predetermined specific gravity and that the battery is therefore not currently in need of recharging. In the other position, the float is guided by the cage downwardly and away from the tip so that it is no longer viewable through the indicating surface. This indicates that the electrolyte specific gravity is now below the predetermined value and that the battery is in need of recharging.

Such hydrometers have been found to be very accurate because the specific gravity of a battery electrolyte exhibits the most reliable relationship to the state of charge of a battery. However, hydrometers of this type are not suited for remote indication, as for example, on the dashboard of an automobile or the like. Further, they indicate only two states of battery charge, one where the battery requires recharging, and the other where the battery has adequate charge.

In an attempt to overcome these deficiencies, hydrometers have been proposed which utilize the same float technique. These hydrometers incorporate a light source and detector to remotely indicate which of the two positions the float is at. On such hydrometer is fully described and claimed in U.S. Pat. No. 3,954,010 which is assigned to the assignee of the present invention. In one position, the float totally blocks the light to the detector and in the other position, the float is out of the way of the light. While monitors of this type do provide remote indication, they still provide an indication of only the two battery charge states indicated by the first mentioned hydrometers.

With renewed interest in battery powered vehicles of all types, there has become a recognized need for an even more improved battery hydrometer which not only provides for remote indication, but which also provides an analog output. Most desirably, an analog output should indicate every battery charge state between and including full battery charge and no battery charge. As a result, such a battery hydrometer would facilitate the use of a remote dashboard meter capable of indicating energy consumption in a manner similar to conventional fuel guages.

It is therefore a general object of the present invention to provide a new and improved battery hydrometer.

It is a further object of the present invention to provide a battery hydrometer which facilitates remote indication while also providing an analog output signal having a magnitude related to the state of charge of a battery.

SUMMARY OF THE INVENTION

The present invention therefore provides a hydrometer for providing an analog indication of the specific gravity of a liquid. The hydrometer includes radiation source means for emitting a detectable beam of radiation, means arranged to be disposed within the liquid for continuously modulating the beam of radiation of the source in response to the specific gravity of the liquid, and detecting means arranged to receive the modulated beam for providing an electrical signal continuously varying in magnitude responsive to the modulated beam of radiation.

The invention further provides a battery hydrometer for providing an analog electrical signal responsive to the specific gravity of a battery electrolyte. The battery hydrometer includes a housing having a pair of sealed housing portions separated by an open intermediate space, a radiation source within one housing portion for projecting a beam of radiation through the space toward the other housing portion, and a piston member within the space arranged to be submerged below the surface of the electrolyte and adapted to continuously modulate the cross-sectional area of the beam of radiation responsive to the specific gravity of the electrolyte. The hydrometer further includes radiation detector means within the other housing portion for providing an analog electrical signal continuously varying in magnitude responsive to the modulated beam of radiation.

BRIEF DESCRIPTION OF THE DRAWING

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a side-plan view, partly in cross-section, of a battery hydrometer embodying the present invention.

DESCRIPTION OF THE PREFERRED EMBODIMENT

Referring now to the sole FIGURE, a storage battery (10) is shown utilizing a battery hydrometer (12) embodying the present invention for monitoring the state of charge of the battery (10). The battery (10) may be of the type commonly referred to as a lead acid battery having a liquid electrolyte (14) comprising a solution of sulphuric acid. As well known, sulphuric acid electrolytes exhibit variations in specific gravity with variations in battery charge. More specifically, as the state of charge of the battery (10) decreases, the specific gravity of the electrolyte (14) will also decrease.

The battery hydrometer (12) includes a housing (16) which is formed from a suitable material, such as a plastic, which will not be attacked by the sulphuric acid electrolyte (14). The housing (16) is either secured or integral to a fluid cap (18) which is cylindrical in shape and which includes external ribs (20) for being frictionally received in sealing relationship with a corresponding opening (22) of the battery (10).

The housing (16) includes a pair of sealed housing portions (24) and (26) which are separated by an opened intermediate space (28). At the lower most extent of the housing (16), the housing (16) includes a bottom wall (30). The bottom wall (30) has an aperture (32) aligned with the open space (28) to permit the electrolyte (14) to fill the open space (28) up to the surface (15) of the electrolyte as illustrated.

The cap (18) includes a plurality of external terminals (34, 36, 38, and 40) and a corresponding plurality of terminals (44, 46, 48, and 50) which are internal to the housing (16). The terminals (34, 36, 38, and 40) are individually electrically coupled to the terminals (44, 46, 48, and 50) respectively.

Within the housing portion (24) there is disposed a radiation source (52) which may take the form of an incandescent light bulb or an infra-red light emitting diode. The radiation source (52) is of the type which provides a relatively narrow beam of radiation (54). Within the inner wall of the housing portion (24) adjacent the open space (28), there is provided a lens means (56). The lens means (56) is preferably a double lens system which separates the narrow beam (54) to provide a relatively broad beam of detectable radiation (58).

Within the other housing portion (26) there is disposed a radiation detector (60) of the type capable of detecting the radiation of the beam (58). In the case of an infra-red source (52), the detector (16) may, for example, be a photo transistor or the like.

Within the inner wall of the housing portion (26) adjacent the open space (28) there is provided a second lens means (62) which again may take the form of a double lens system for converging the beam (58) to another relatively narrow beam (64) for focusing all of the radiation of the beam (58) received by the lens means (62) onto the detector (60).

The radiation source (52) is coupled to the terminals (44) and (46) which are in turn coupled to the external terminals (34) and (36). The radiation source (52) may therefore be coupled to an electrical potential at the terminals (34) and (36) for powering the source (52). This of course is necessary when the radiation source (52) is in the form of an infrared light emitting diode or an incandescent light bulb.

In a similar manner, the detector (60) may be coupled to the external terminals (38) and (40) by being intermediately coupled to the terminals (48) and (50). In the case of a photo transistor for the detector (60), the terminals (38) and (40) would be coupled to a suitable electrical circuit where the current conducted by the photo transistor (60) may be sensed to provide an electrical signal. Such circuits are well known in the art and need not be described herein. Suffice it to say that the amount of current conducted by the photo transistor of detector (60) is dependent upon the amount of light which it receives.

Disposed within the open space (28) there is a piston member (70). The piston member preferably has a specific gravity much lower than that of the electrolyte's lowest value and may, for example, be hollow in structure formed from a plastic material which is not attacked by the sulphuric acid electrolyte (14). However, the piston member (70) could just as well be formed from a solid material.

The piston member (70) is suspended within the open space (29) by a spring means in the form of a coiled spring (72). The spring (72) may be formed from a nickel alloy which is not attacked by the sulphuric acid electrolyte (14). Also, the spring (72) should have a relatively low spring constant for reasons to be explained hereinafter.

In operation, when the battery hydrometer (16) is inserted through the opening (22) of the battery (10) and disposed in its position as illustrated, the lower extent of the housing (16) will be submerged beneath the surface (15) of the electrolyte (14) so that the open space (28) will fill with electrolyte to the level (15). As a result, the piston member (70) will be fully submerged beneath the surface of the electrolyte. However, because the housing portions (24) and (26) are sealed, the radiation source (52) and the detector (60) will not be exposed to the sulphuric acid. Of course, the lens means (56) and (62) will likewise not be exposed to the sulphuric acid.

If the barrery (10) is fully charged, the specific gravity of the electrolyte (14) will be at its highest value and exert a buoyant force against the piston (70) to force the piston (70) upwardly in vertical movement within the open space (28). However, the spring (72) exerts a substantially equal compressive force against the piston member (70) against which the electrolyte (14) must act. Hence, when the battery is fully charged, the piston member (70) will be in equilibrium at the position indicated by its solid line position. In this position, either all or substantially all of the radiation beam (58) will be transmitted from the lens means (56) to the lens means (56) to the lens means (62) and thereafter converged to the narrow beam (64) for focusing upon the detector (60). The photo transistor of the detector (60) will thereby provide its maximum current to be sensed by the external circuitry for indication on an analog meter or the like.

As the battery discharges, the specific gravity of the electrolyte (14) will decrease so that the buoyant force exerted by the electrolyte against the piston member (70) will likewise decrease. Hence, as the specific gravity of the electrolyte (14) decreases, the piston member (70) will move downwardly within the vertical opening (28) to intercept increasing cross-sectional areas of the radiation beam (58). As this occurs, the photo transistor of the detector (60) will receive continuously decreasing amounts of light and will therefore in turn provide a continuously decreasing output current. This continuously decreasing current or electrical signal may be displayed on the aforementioned analog output meter.

When the battery becomes fully discharged, the piston member (70) will have moved vertically downwardly to its dashed line position. In this position, all of the beam (58) will be intercepted by the piston member (70) so that no light will reach the photo transistor of detector (60). Hence, the photo transistor will conduct its minimum current to indicate on the external meter that the battery (10) is fully discharged.

From the foregoing, it can be appreciated that the battery hydrometer illustrated in the sole FIGURE not only provides a remote indication of the state of charge of the battery (10), but additionally, provides an analog indication or electrical signal output for indication on a remote analog meter. As a result, the state of charge of the battery (10) may be monitored continuously from its fully charged state to its fully discharged state in a manner similar to conventional fuel guages.

Referring again to the sole FIGURE, it will be noted that the aperture (32) of the bottom wall (30) is dimensioned to be smaller in size than the piston member (70). This precludes the piston member (70) from exiting the open space (28) before the hydrometer (12) is placed into its operating environment or after the battery hydrometer is removed from the battery (10).

Additionally, while the battery hydrometer of the instant embodiment of the present invention incorporates as infra-red light emitting diode for the radiation source (52), it will be understood by those skilled in the art that other radiation sources may be utilized as well. For example, the radiation source (52) could be an atomic radiation source which inherently provides a broad beam of radiation. Use of such a source would render the lens system (56) unnecessary as well as external connections to a suitable power source for powering the radiation source. Furthermore, detectors other than photo transistors may be utilized for the radiation detectors (60). Each detector will depend upon a particular spectrum characteristics of the radiation provided by the various radiation sources as can be appreciated by those skilled in the art.

While a particular embodiment of the present invention has been shown and described, modifications may be made, and it is therefore intended to cover in the appended claims all such changes and modifications which fall within the true spirit and scope of the invention as defined by said claims.

I claim:

1. A hydrometer for providing an analog indication of the specific gravity of a liquid comprising radiation source means for emitting a detectable beam of radiation; means arranged to be disposed within the liquid for continuously modulating the beam of radiation of said source in response to the specific gravity of the liquid; and detecting means arranged to receive said modulated beam for providing an electrical signal continuously varying in magnitude responsive to said modulated beam of radiation.

2. A hydrometer as defined in claim 1 wherein said modulating means comprises a piston member arranged to be submerged within the liquid and arranged to intercept said beam of radiation and vary the cross-sectional area of said beam in varying amounts responsive to the specific gravity of the liquid.

3. A hydrometer as defined in claim 2 wherein said radiation source means includes a radiation source for providing a narrow beam of radiation and a lens means for broadening the cross-sectional area of said narrow beam.

4. A hydrometer as defined in claim 3 wherein said detecting means includes a radiation detector and second lens means for receiving and focusing the unintercepted portion of said broadened beam onto said radiation detector.

5. A hydrometer as defined in claim 4 wherein said radiation source is arranged for providing infra-red light radiation.

6. A hydrometer as defined in claim 5 wherein said radiation detector comprises a photo transistor.

7. A hydrometer as defined in claim 2 further comprising spring means for suspending said piston member within the liquid to exert a compressive force upon said piston member against which the specific gravity of the liquid must act.

8. A hydrometer as defined in claim 7 wherein said spring means comprises a coiled spring formed from a nickel alloy material.

9. A battery hydrometer for providing an analog indication of the specific gravity of a battery electrolyte, comprising: a source of radiation for providing a detectable beam of radiation having a relatively broad cross-sectional area; a piston member arranged to be submerged within the electrolyte and to intercept said beam of radiation for continuously varying the effective transmitted cross-sectional area of said beam responsive to the specific gravity of the electrolyte, and detector means arranged to receive the effective transmitted cross-sectional area of said beam and to provide an electrical signal having a magnitude continuously varying with the received cross-sectional area of said beam.

10. A hydrometer as defined in claim 9 wherein said piston member is arranged to move vertically within the path of said beam of radiation for varying the cross-sectional area of said beam transmitted to said detector means responsive to the specific gravity of the electrolyte.

11. A hydrometer as defined in claim 10 further comprising spring means for vertically suspending said piston member within said electrolyte and for exerting a compressive force upon said piston member against which the electrolyte must act for vertically moving said piston member within the path of said beam.

12. A hydrometer as defined in claim 11 wherein said spring means comprises a coiled spring formed from a nickel material.

13. A hydrometer as defined in claim 9 wherein said radiation source includes lens means for providing said relatively broad cross-sectional beam.

14. A hydrometer as defined in claim 9 wherein said detector means includes a radiation detector and lens means for receiving and focusing the transmitted beam onto said radiation detector.

15. A hydrometer as defined in claim 14 wherein said radiation detector comprises a phototransistor.

16. A battery hydrometer for providing an analog electrical signal responsive to the specific gravity of a battery electrolyte, comprising: a housing having a pair of sealed housing portions separated by an opened intermediate space; a radiation source within one said housing portion for projecting a beam of radiation through said space toward the other said housing portion; a piston member within said space arranged to be submerged below the surface of the electrolyte and adapted to continuously modulate the cross-sectional area of said beam of radiation responsive to the specific gravity of the electrolyte; and radiation detector means within said other housing portion for providing an analog electrical signal continously varying in magnitude responsive to said modulated beam of radiation.

17. A battery hydrometer as defined in claim 16 further comprising spring means suspending said piston member within said space for vertical movement between said radiation source and said radiation detector means.

18. A battery hydrometer as defined in claim 16 wherein said housing further includes a bottom wall having an aperture aligned with said opened spaced and dimensioned smaller than said piston member to permit said piston member to be submerged within the electrolyte while preventing said piston member from exiting said space when the level of the electrolyte falls below said bottom wall.

* * * * *